United States Patent [19]

Fukuda et al.

[11] 4,284,724

[45] Aug. 18, 1981

[54] METHOD OF HIGHLY CONCENTRATED CULTIVATION OF YEASTS

[76] Inventors: Hideki Fukuda, 1696-2, Honjo, Harima-cho, Kako-gun, Hyogo-ken; Takeshi Shiotani, 2-63, Okihama-cho, Takasago-cho, Takasago-shi, Hyogo-ken; Wataru Okada, 4-2, Takakura-dai, Suma-ku, Kobe-shi, Hyogo-ken, all of Japan

[21] Appl. No.: 5,225

[22] Filed: Jan. 22, 1979

Related U.S. Application Data

[63] Continuation of Ser. No. 827,541, Aug. 25, 1977, abandoned.

[51] Int. Cl.$^3$ ............................................. C12N 1/16
[52] U.S. Cl. ................................... 435/255; 435/256; 435/800; 435/804; 435/813; 435/940
[58] Field of Search ................. 435/68, 255, 800, 801, 435/804, 813, 940

[56] References Cited

U.S. PATENT DOCUMENTS

| | | | |
|---|---|---|---|
| 3,186,917 | 6/1965 | Gerhardt et al. | 195/109 |
| 3,418,208 | 12/1968 | Coty | 195/115 X |
| 3,847,739 | 11/1974 | Champagnat et al. | 195/82 X |
| 3,887,435 | 6/1975 | Nakamura et al. | 195/82 |
| 3,929,578 | 12/1975 | Urakami | 195/82 X |
| 3,940,492 | 2/1976 | Ehnstrom | 195/115 X |
| 3,966,554 | 6/1976 | Vass et al. | 195/82 X |
| 4,028,182 | 6/1977 | Zajic et al. | 195/28 R |
| 4,062,727 | 12/1977 | Srinivasan et al. | 195/82 |

FOREIGN PATENT DOCUMENTS 51-9833  3/1976  Japan.

OTHER PUBLICATIONS

Gerhardt et al., "Dialysis Flask for Concentrated Culture of Microorganisms", J. Bacteriology vol. 86, pp. 919-928, (1963).

*Primary Examiner*—R. B. Penland

[57] ABSTRACT

A broth containing yeast cells is continuously or intermittently removed from a fermentor. Then, yeast cells are separated from the filtrate using a cell separator, or further washed with water. Then, the yeast cells so obtained are recycled to the fermentor, whereby yeasts are cultivated at a high cell concentration of from 6% to about 20% based on dry weight. As discussed herein, by removing the filtrate from the cultivation system, there is no accumulation of metabolites and salts prohibiting the cultivation of yeasts, and further the growth of miscellaneous microorganisms which interfere with yeast cell growth, is surprisingly suppressed.

6 Claims, 4 Drawing Figures

METHOD OF HIGHLY CONCENTRATED CULTIVATION OF YEASTS

This is a continuation of Ser. No. 827,541, filed Aug. 25, 1977 and now abandoned.

BACKGROUND OF THE INVENTION

The present invention relates to a method of aerobic cultivation of yeasts, and more particularly to such a method wherein high cell concentration is employed during cultivation.

In the prior art, unsuccessful attempts have been made to enhance cell concentration in an aerobic cultivation method. These attempts have principally focused on nutrient supply control and oxygen supply control. The latter methods involved development of a fermentor which improved the speed of oxygen supply, a method using oxygen as proposed in Japanese Pat. No. 9833/1976 and the like. However, all of the prior methods were found deficient in one way or another, and did not successfully enhance cell concentration.

In analyzing the failure of the previous methods, it appears that a number of factors prohibit or retard multiplication of yeast cells in an aerobic cultivation; such as (1) shortage of a main carbon source, inorganic salts or other nutrients; (2) shortage of oxygen; (3) accumulation of metabolites of yeasts; and (4) accumulation of salts. Thus, eliminating the first two factors, namely, (1) and (2), would still not satisfactorily improve cell multiplication and cell concentration, since cultivation is suppressed by the other factors (3) and (4) mentioned above.

SUMMARY OF THE INVENTION

It is an object of the present invention to provide a method of yeast cultivation wherein cell concentration is enhanced.

Another object of the present invention is to provide a cultivation method wherein accumulation of metabolites and salts is substantially eliminated.

Still another object is to provide a cultivation method wherein growth of microorganisms is suppressed, and high quality yeast products are produced.

Another object is to rationalize cultivation equipment and wast water treatment systems used for such cultivation of yeasts.

Other objects are to eliminate or substantially reduce the aforementioned disadvantages and deficiencies of the prior art.

The foregoing and other objects of the invention are attained in the inventive method wherein yeast cells in a cultivating broth comprising a main carbon source and other nutrients and additives, are cultivated in a fermentor; then the broth containing the yeast cells are removed from the fermentor and the yeast cells ares separated from the filtrate; and then after cooling, the yeast cells are recirculated to the fermentor. The yeast cell concentration in the fermentor is brought up preferably to a range of at least 6% to about 20% based on dry weight. By removing the filtrate from the cultivation system as discussed herein and hence making the cell concentration within the aforementioned range, and cultivating yeast cells in such high cell concentration broth, it was discovered that surprisingly growth of miscellaneous microorganisms were effectively suppressed, and further that surprizingly, there were no accumulations of metabolites and salts. Yield of yeast cells was thus substantially and unexpectedly increased and quality was greatly increased. The yeast cell cultivation may be batchwise or continuously carried out. When the batch process is used, the start up concentration of yeast cells is preferably more than 0.1%, and more preferably more than 0.5%. The separation of yeast cells and filtrate may be by such methods as centrifugal separators or membrane separators. When centrifugal separators are used, water up to twice the volume of the filtrate may be used. When a membrance separator is used, the amount of water used may be from two to five times the amount of filtrate volume. The amount of filtrate after separating of yeast cells may be from 0.3 to 4 times the amount of feed liquor.

A feature of the invention is the yeast cell concentration within the range of 6% to 20% based on dry weight, and more preferably above 8%.

Another feature is the starting up cell concentration when batch process is used, of above 0.1% and more preferably above 0.5%, based on dry weight.

A further feature is the aeration of the cultivating broth with air containing at least 30% oxygen.

Another feature is pressurizing of the fermentor to a pressure within the range of 0.5 to 5.0 Kg/cm$^2$G.

A further feature is removing from the fermentor broth in sufficient quantity that the amount of filtrate after separation of the yeast cells is from 0.3 to 4.0 times the total amount of feed liquor.

Another feature is washing the yeast cells with water in amounts ranging from zero to twice the volume of filtrate when a centrifugal separator is used.

A further feature is use of a membrane separator and washing the yeast cells with water in amounts from 2 to 5 times the volume of the filtrate.

DETAILED DESCRIPTION OF PREFERRED EMBODIMENTS

In an attempt to resolve the problems of accumulation of metabolites of yeasts and accumulation of salts, the present inventors have discovered that after cultivation of yeast cells in a fermentor, if the broth containing the yeast cells and filtrate were separated and the separated yeast cells were recirculated back to the fermentor, it was possible to raise the cell concentration.

Accumulation of metabolites of yeasts depends upon such factors as kind of yeast, main carbon source, cultivation conditions and the like. For example, in the case of bakers' yeast (Saccharomyces cerevisiae) wherein sugar is used as a main carbon source, alcohols, organic acids and other metabolites are metabolized in the broth. As these metabolites accumulate, the quality of the product is lowered and the multiplication of yeast is lowered. This situation also applies for yeast of other genus, and use of other main carbon sources.

Accumulation of salts, depends upon various factors. For example, when cultivation is performed using molasses as a main carbon source, a variety of salts and sugars unassimilated by the yeasts, which are contained in the molasses, accumulate in the broth and detrimentally effect multiplication of the yeasts.

The present invention resolves both of these problems of accumulation of metabolites and salts.

When the problem of shortage of oxygen is also desired to be resolved, it is possible to aerate with a highly concentrated oxygen containing air, or to pressurize the fermentor, or to employe a fermentor having a large oxygen capacity. Hence, according to the present invention, various industrial and practical advantages, including rationalization of fermentation equipment and treatment equipment for waste water, and the like, accrue.

The present inventors approached the problem with the idea that cultivation effected at high concentrations of cells would reduce multiplication of miscellaneous microorganisms other than the desired yeasts. In general, when miscellaneous microorganisms intrude into the broth, they grow to suppress yeasts and thus the product obtained is degraded in quality. In a continuous cultivation method, the miscellaneous microorganisms limit the period of continuous cultivation. It is thus of specific importance in the field of fermentation to prevent the multiplication of miscellaneous microorganisms. The present inventors have successfully done this and have advanced the art in a substantial and unexpected manner.

Upon analyzing various experiments, the inventors discovered that multiplication of miscellaneous microorganisms is reduced as the cell concentration of the desired yeast is increased, such as by separating and removing the filtrate from the cultivation system as discussed herein and the multiplication of miscellaneous microorganisms is markedly and unexpectedly suppressed at the cell concentration of at least 6% based on dry weight.

Figure 1:
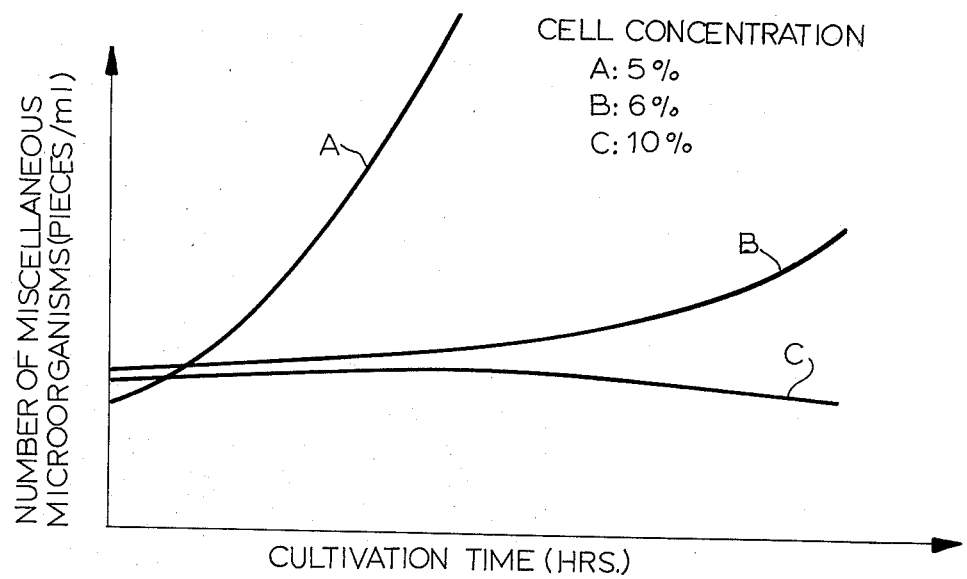
FIG. 1 depicts a graph showing growth of miscellaneous microorganisms against time for various different cell concentrations.

Turning now to FIG. 1, there is depicted a graph showing the relationship between the number of miscellaneous microorganisms and the time of cultivation, using a number of different cell concentrations. Various yeasts were cultivated using a single fermentor and change in the number of miscellaneous microorganisms with the lapse of time was observed with a microscope. The results were plotted as a general trend. On the abscissa is the cultivation time and on the ordinate is the number of miscellaneous microorganisms. FIG. 1 shows that the effect of preventing growth of miscellaneous microorganisms can be produced with cell concentration of more than 6% based on dry weight, and more preferably more than 8% based on dry weight. The upper limit of the cell concentration cannot be uniformly stated because it depends upon such factors as kind of yeasts, and especially the size. However, the upper limit may be approximated at 20% based on dry weight.

When the present invention is applied to a batchwise cultivation, it is preferred to begin the cultivation at a higher starting-up concentration than usual. To carry out the cultivation up to a cell concentration of 6%, the cultivation time is prolonged as compared with the case where the cultivation is completed at a low cell concentration. For this reason, if starting up concentration is low, it takes a longer time to reach the required cell concentration to sufficiently suppress the growth of miscellaneous microorganisms, and during the time of build up to that required cell concentration, miscellaneous microorganisms will continue to multiple. Thus, the effect of suppressing miscellaneous microorganisms is reduced. It is therefore necessary to begin cultivation at a starting-up cell concentration of more than 0.1%, and more preferably more than 0.5% based on dry weight.

In the present invention, by separating the filtrate from the cultivation system in the manner discussed the number of yeast cells is increased sufficiently to suppress the growth of miscellaneous microorganisms. By doing so, the present invention succeeded in eliminating the aforementioned factors which usually prevented the multiplication of yeast cells. Thus, the present invention is advantageously of great industrial value. Also, the quality of the obtained product is greatly improved and the time of continuous cultivation is lengthed.

Yeasts used in the present invention may include Saccharomyces; Candida; Rhodotorula; Torulopsis; Hansenula; Pichia; Debaryomyces; Schizosaccharomyces; Trichosporon and any other yeast capable of assimilating sugars such as glucose and molasses; hydrocarbons such as n-paraffin; alcohols such as ethanol and methanol; carboxylic acids such as acetic acid, ethylacetic acid and succinic acid; and fats and oils such as soybean oil and fish oil. These yeasts may be used singly or in combination of two or more.

The main carbon sources used in the present invention may include sugars, hydrocarbons, alcohols, carboxylic acids, fats and oils and the like. They may be employed singly or in combination of two or more. The present invention is applicable to all types of fermentors, such as a fermentor provided with an agitator, a fermentor of the tower type, and the like.

Figure 2:
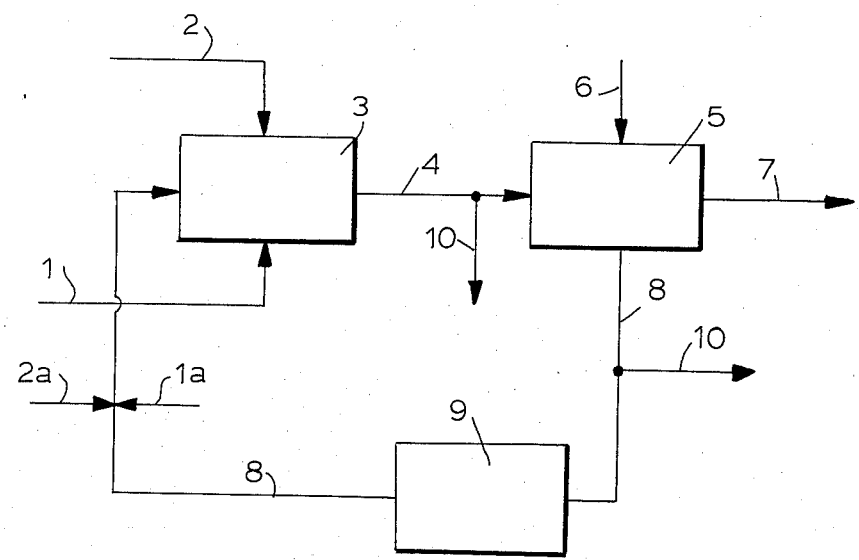
FIG. 2 depicts a flow diagram showing the different steps of the invention.

Turning now to FIG. 2, which is flow diagram illustrating a preferred embodiment of the invention, there is depicted an air feed line 1 and a feed line 2 for feeding in a main carbon source and other nutrients both of which lines supply fermentor 3. Broth is taken from fermentor 3 out through a line 4 and led to a cell separator 5 wherein yeast cells are separated and then recycled through a line 8 via cooling means 9, to fermentor 3.

Inhibiting substances such as metabolites and salts accumulated in the fermentor 3 are separated by separator 5. Line 6 supplies water for washing the cells, to separator 5, and line 7 exiting from separator 5 is used to remove the filtrate.

When fermentor lacks oxygen, air with a high concentration of oxygen is supplied through line 1 to aerate the broth. In order to prevent detrimental effects of so-called oxygen toxicity, care must be taken to carry out cultivation at the most suitable range of dissolved oxygen concentration, which depends upon kind of yeast, main carbon source and the like. It is preferred to use air containing more than 30% oxygen, and more preferably 30 to 60% oxygen. Air and oxygen may, of course, be separately supplied to the fermentor through separate lines. The fermentor 3 may be under effective pressure for the purpose of increasing oxygen supply; the pressure may be in the range of from 0.5 to about 5.0 Kg/cm$^2$.G. Pressure without this range is not advantageous since such higher pressure requires a pressure-proof fermentor and the addition of an aeration compressor.

The cell separator 5 may be a centrifugal separator such as that used for cell separation, or a membrane separator, or other similar cell separator. When a membrane separator is used, permeable speed is greatly lowered with increased cell concentration so that is is recommended to conduct separation by diluting the broth with washing water. The amount of broth taken out and the amount of washing water are decided upon according to the kind of yeasts, main carbon source and the degree of metabolites accumulated. The broth is preferably removed from the fermentor 3 in such a manner that the amount of filtrate from the cell separator 5 is within the range of from 0.3 to 4 times the volume of the total amount of feed liquor containing the main carbon source, other nutrients and diluting water and the like. Washing water in amounts of twice the volume of filtrate or less may be effectively used. When using a membrane separator, however, about two to five times the volume of filtrate is preferred. The broth may be removed continously or intermittently, for example, every hour. Thus, a optional manner may be selected according to the kind of yeast, main carbon source, continuous or batch-wise cultivation and the like.

As washing water, an aseptic water may be preferably employed for the purpose of avoiding contamination of miscellaneous microorganisms. Such aseptic water may be obtained by passing ordinary water through a sterilization filter or by heating to sterize.

The cooler 9 may be used to remove heat, which the yeast cells generate during cultivation in the fermentor 3. The cooler 9 may be of the plate type, tubular type or any other known heat exchanger. In cases where the generation of heat is small, the cooler 9 may not be required. In continous cultivation, the broth may be removed through a line 10 located either in front of or in back of the cell separator 5. A main carbon source and other nutrients may be added through a line 2a to the recycling yeasts separated from the filtrate by separator 5, before being recycled to the fermentor 3., as depicted. Further, in order to prevent the yeast cells from becoming less active, air may be added through line 1a to the recycling yeast cells.

Figure 3:
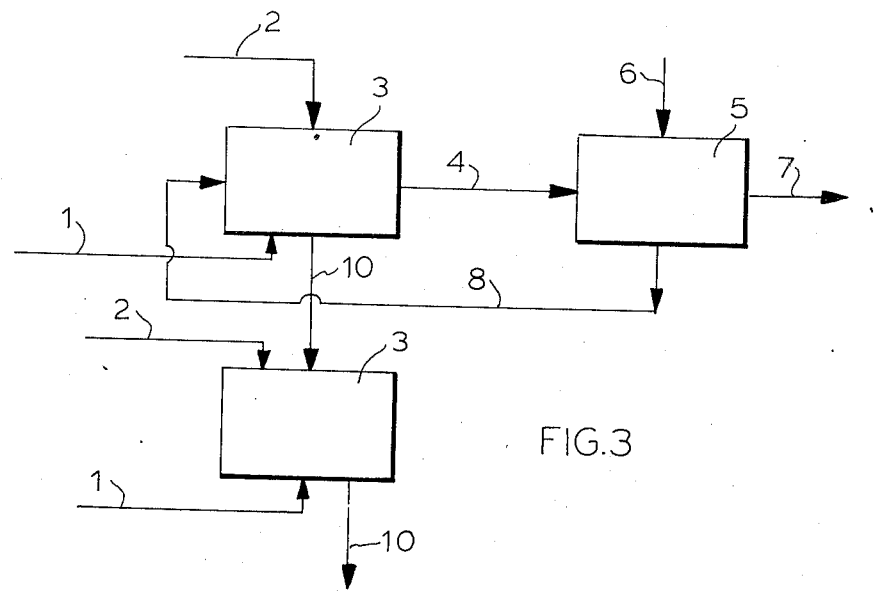
FIG. 3 depicts a flow diagram showing the different steps of the invention and employing a second fermentor.

The present invention may be used for continuous cultivation using multiple fermentors. In FIG. 3, a second fermentor, also labelled 3, is employed with broth being removed from the first fermentor, after repeated yeast cell cultivations and after recirculation of the separated cells, through line 10. Then, the second fermentor further cultivates the yeast cells before removing through line 10 exiting from the second fermentor 3. A main carbon source, other nutrients and air may be added to the recycled yeast cells in the second fermentor.

Figure 4:
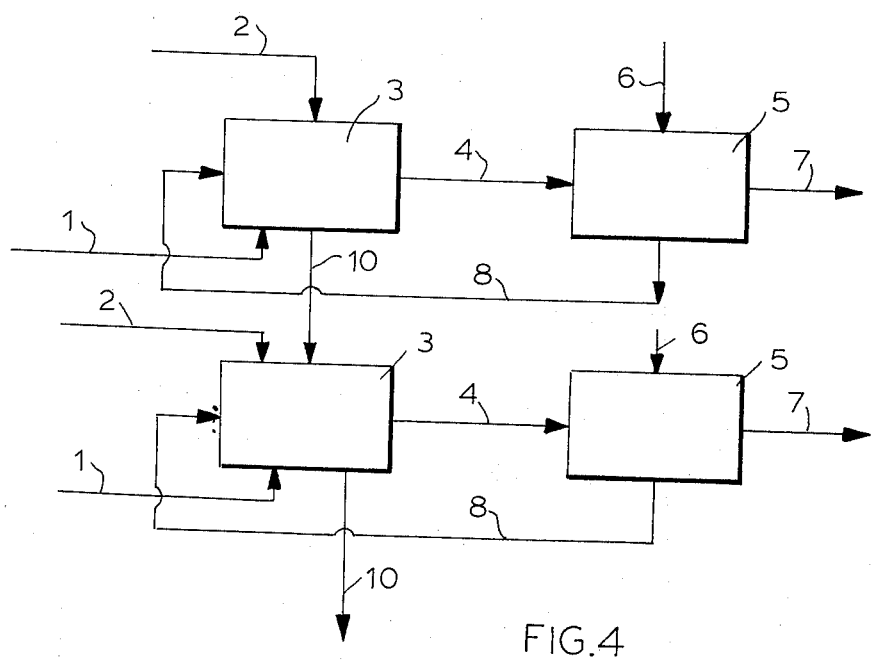
FIG. 4 depicts a flow diagram showing the different steps of the invention and employing double sets of fermentors and separators.

In FIG. 4, there is depicted a double line of similar fermentors, separators and feedback circuits. The operation is similar to that of the single line system of FIG. 1. After the first recirculation of the separated cells, the broth is removed from fermentor 3 of the upper line and supplied to fermentor 3 of the lower line, wherein further cultivation is carried out, and then, the resulting broth is supplied to the separator 5 of the lower line, and recirculated is the separated yeast cells as done with the FIG. 1 embodiment.

This invention will be illustrated hereinbelow in more detail by way of examples, which examples are not to be construed in any manner to be limiting of the invention.

EXAMPLE 1 AND COMPARATIVE EXAMPLE 1.

Yeast Employed

Saccharomyces cerevisiae (Bakers Yeast)

Main Carbon Source and Nutrients

A 40% aqueous solution of molasses (produced in the Philippines) was employed as a main carbon source; and ammonia sulphate and urea as a nitrogen source, and phosphoric acid as a phosphorus source were further used.

Cultivation Conditions

A 30 liter jar fermentor was used. The temperature was maintained at 33° C. pH value was adjusted to the range of from 4.5 to 5.0 using a 10% aqueous ammonia. Aeration was carried out at the rate of 20 Nl/min. and stirring was conducted at the rate of 400 r.p.m. Aeration was controlled in such a manner that the partial pressure of oxygen was increased using an oxygen bomb and the dissolved oxygen concentration was maintained in the range of from 2 to 7 ppm. In this case, the total amount of air and oxygen was set at 20 Nl/min.

Cultivation Method 400 ml of a 46% aqueous solution of urea, 80 g of ammonia sulphate and 60 g of a 85% aqueous solution of phosphoric acid were charged prior to cultivation into a 30 liter jar fermentor. The starting-up amount of liquor was set at 10 liter and the starting-up cell concentration was set at 1%, measured as dry weight basis; the yeast cells being dried for 7 hours at 110° C., then measured. The addition of main carbon source was executed sufficiently depending on the degree of multiplication, in such a manner that the concentration of ethanol in the broth was maintained in the range of from 500 to 3,000 ppm (measured using a gas chromatography). The cultivation was carried out for 16 hours in a batchwise operation. When 8 hours passed, the broth was partly taken out, then the yeast cells were separated, using a centrifugal separator (WESTPHALIA type LWA 205), for 20 minutes. Then, the yeast cells so separated were recycled to the fermentor. The cultivation was thus continued. The separation of yeast cells was performed every hour up to the completion of cultivation in such manner that the amount of liquor of main carbon sources added in each hour was almost equal to the amount of liquor filtered off with the centrifugal separator, and containing no yeast cells.

As the comparative example 1, the cultivation was carried out under the same conditions as just discussed, except that no separation of yeast cells was effected.

Cultivation Results

The yeast products obtained were observed and tabulated in Table 1 hereinbelow. The final amounts of yeasts were measured on a dry weight basis, wherein the yeasts obtained were dried at 110° C. for 7 hours, then measured.

TABLE 1

| | Ex. 1 | Comp. Ex. 1 |
|---|---|---|
| Final amount yeasts (g) | 2,125 | 1,260 |
| Final cell concentration (%) | 12.5 | 7.0 |
| Yield* (%) | 40 | 36 |
| Number of miscellaneous microorganisms at the | less than $10^6$ | $10^8$ |

TABLE 1-continued

|  | Ex. 1 | Comp. Ex. 1 |
|---|---|---|
| final stage (pieces/ml) |  |  |

Note:
*The yield was represented by percent of yeast cells dried per the amount of sugars added.

EXAMPLE 2 AND COMPARATIVE EXAMPLE 2

Yeast Employed

The same as in Example 1.

Main CArbon Soure and Nutrients

The same as in Example 1.

Cultivation Conditions

The same as in Example 1, except that the stirring was conducted at the rate of 700 r.p.m. and the jar fermentor was under pressure of 1 Kg/cm$^2$.G.

Cultivation Method

The same as in Example 1.

Comparative Example 2 was effected under the same conditions except that the yeast cells were not subjected to the separation step.

Cultivation results:

TABLE 2

|  | Ex. 2 | Comp. Ex. 2 |
|---|---|---|
| Final amount of yeasts (g) | 2,210 | 1,200 |
| Final cell Concentration (%) | 13.0 | 6.7 |
| Yield (%) | 41 | 34 |

EXAMPLE 3 AND COMPARATIVE EXAMPLE 3

Yeast Employed

Candida utilis (IAM 4215)

Main Carbon Source and Nutrients

A 30% aqueous solution of molasses (produced in the Philippines) was used and other nutrients were the same as in Example 1.

Cultivation conditions

Using a 30 liter jar fermentor, the cultivation was continuously executed at 28° C. and the pH was adjusted t the range of from 4.5 to 5.0. Aeration and stirring conditions were the same as in Example 1.

Cultivation Method 0.5% of urea; 0.2% of ammonium sulphate and 0.2% of phosphoric acid were added to a 30% aqueous solution of molasses to prepare a feed liquor. The feed liquor thus obtained was continuously supplied to the fermentor at the rate of 3 l/hr. adjusting the amount of liquid in the fermentor to about 20 liter. The broth was continously taken out at the rate of 3 l/hr. using a pump. Then, the yeast cells were separated using a centrifugal separator, wherein the separation was carried out while mixing the broth taken out with washing water in amount of 3 l/hr. After separation and washing, the yeast cells were recycled to the jar fermentor, then the same cycle was repeated.

In contrast, Comparative Example 3 was conducted similary, except for the carrying out of the separation steps.

Cultivation Results

It was first assured that the continuous cultivation had reached steady state. Then, the cell concentration was measured on a dry weight (using the procedures as mentioned above) and the growth rate and yield were calculated. The results are set forth in Table 3 hereinbelow.

TABLE 3

|  | Ex. 3 | Comp. Ex. 3 |
|---|---|---|
| Growth rate (g/hr) | 360 | 220 |
| cell concentration in the fermentor (%) | 12.0 | 7.3 |
| Yield (%) | 40 | 24.4 |
| Number of miscellaneous microorganisms after 40 hours (pieces/ml) | less than 10$^6$ | 3 × 10$^8$ |

EXAMPLE 4 AND COMPARATIVE EXAMPLE 4

Yeast Employed

Candida utilis (IAM 4215)

Main carbon Source and Nutrients

As a main carbon source 30% ethanol was employed; and other nutrients set forth below were used.

| | | |
|---|---|---|
| H$_3$PO$_4$; 4,000 ppm | KCl; 4,000 ppm | MgSO$_4$; 4,000 ppm |
| Ammonium sulphate, 500 ppm | NaCl: 100 ppm | CaCl$_2$; 200 ppm |
| FeSO$_4$ . 7H$_2$O: 200 ppm | ZnSO$_4$ . 7H$_2$O; 200 ppm | MnSO$_4$ . 6H$_2$O: 20 ppm |
| CuSO$_4$ . 5H$_2$O; 4 ppm | Vitamin B$_1$; 2 ppm | Biotin; 1 ppm |

Cultivation Conditions

Using a 30 liter jar fermentor, the batch wise cultivation was effected at 33° C. and at pH 5.0. Aeration and stirring were the same as in Example 1.

Cultivation Method

The nutrients comprising the aforementioned nutrients were introduced into a 30 liter jar fermentor and the cultivation was bgun at a starting-up concentration of 1% based on dry weight. The amin carbon source was added in such a manner that the concentration of ethanol in the broth was maintained at the range of from 0.2 to 0.5%. The cultivation was carried out for 18 hours while the separation procedure was being performed as in Example 1.

Comparative Example 4 was executed similarly, except for the separation procedure which was not done.

Cultivation Results

TABLE 4

|  | Ex. 4 | Comp. Ex. 4 |
|---|---|---|
| Final amount yeasts (g) | 1,920 | 1,200 |
| Number of miscellaneous microorganisms at the final stage (pieces/ml) | 1 × 10$^6$ | 8 × 10$^7$ |

EXAMPLE 5 AND COMPARATIVE EXAMPLE 5

Yeast employed

Pichia mogii (IFO 0607)

Main Carbon Source and Nutrient

Soybean oil was used as a main carbon source and other nutrients were the same as in example 1.

Cultivation conditions

The same as in Example 1.

Cultivation Method

The nutrients were charged into 15 liters of starting-up liquor, then the cultivation was conducted batch-wised at 1% starting-up cell concentration. Soybean oil as a main carbon source was added for the concentration of the broth to be kept about 12%. The cultivation was continued for 18 hours. At the 10th hour after the cultivation began, the yeast cells were separated under the same conditions as in Example 1.

Comparative Example 5 was similarly carried out, except without the separation procedures.

Cultivation Results

TABLE 5

|  | Ex. 5 | Comp. Ex. 5 |
| --- | --- | --- |
| Final amount of yeast (g) | 2,100 | 1,400 |

The foregoing description is illustrative of the principles of the invention. Numerous variations and modifications thereof would be apparent to the worker skilled in the art. All such variations and modifications are to be considered to be within the spirit and scope of the invention.

What is claimed is:

1. A method of highly concentrated aerobic cultivation of yeast cells in a batch process using a cultivating system comprising a fermentor and a separator, said method comprising:

cultivating said yeast cells in said fermentor using a feed liquor comprising carbon source, nutrients and diluting water;

setting the starting—up cell concentration at at least 0.1%;

removing continuously or intermittently from said fermentor during the course of cultivation, a broth containing a portion of said yeast cells and feed liquor in such a manner that the amount of filtrate removed from said separator is within the range of from 0.3 to 4 times the volume of said feed liquor fed during the course of cultivation;

separating said broth into yeast cells and filtrate, said filtrate containing growth inhibiting substances;

removing said filtrate from the cultivation system;

recycling the total amount of separated yeast cells to said fermentor wherein cultivation is continuing; and repeating the above steps to bring the final cell concentration between 6% and about 20% thereby to substantially suppress growth of undesired miscellaneous microorgaisms.

2. The method of claim 1, wherein said cell concentration is at least 8% based on dry weight.

3. The method of claim 1, wherein the starting-up cell concentration is at least 0.5%.

4. The method of claim 1, wherein said yeast cells are separated centrifugally and washed with water in amounts up to twice the volume of the filtrate remaining after separating of said yeast cells.

5. The method of claim 1, wherein said yeast cells are separated through a membrane and washed with water in amounts between two to five times the volume of the filtrate remaining after separating of said yeast cells.

6. The method of claim 1, wherein the yeast is at least one member selected from the group consisting of Saccharomyces; Candida; Rhodotorula; Torulopsis; Hansenula; Pichia; Debaryomyces; Schizosaccharomyces and Trichosporon.

* * * * *